(12) United States Patent
Yoshitomo et al.

(10) Patent No.: US 8,563,770 B2
(45) Date of Patent: Oct. 22, 2013

(54) BIS(FORMYLPHENYL) COMPOUND AND NOVEL POLYNUCLEAR POLYPHENOL COMPOUND DERIVED FROM THE SAME

(75) Inventors: Akira Yoshitomo, Wakyama (JP); Tatsuya Iwai, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/555,023

(22) Filed: Jul. 20, 2012

(65) Prior Publication Data

US 2012/0289735 A1 Nov. 15, 2012

Related U.S. Application Data

(63) Continuation of application No. 12/745,367, filed as application No. PCT/JP2008/070324 on Nov. 7, 2008, now abandoned.

(30) Foreign Application Priority Data

Nov. 28, 2007 (JP) .................................. 2007-306710
Apr. 30, 2008 (JP) .................................. 2008-118798

(51) Int. Cl.
| | | |
|---|---|---|
| *C07C 59/40* | (2006.01) | |
| *C07C 62/30* | (2006.01) | |
| *C07C 63/33* | (2006.01) | |

(52) U.S. Cl.
USPC ........................................................ 562/468

(58) Field of Classification Search
None
See application file for complete search history.

(56) References Cited

U.S. PATENT DOCUMENTS 4,163,801 A 8/1979 McGarry et al.

FOREIGN PATENT DOCUMENTS

| JP | 03-200251 A | 9/1991 |
|---|---|---|
| JP | 06-130670 A | 5/1994 |
| JP | 08-193055 A | 7/1996 |
| JP | 2001-142217 A | 5/2001 |
| JP | 2005-099683 A | 4/2005 |
| JP | 2006-267996 A | 10/2006 |
| JP | 2007-039381 A | 2/2007 |
| WO | WO 2006/090757 A1 | 8/2006 |
| WO | WO 2007/034719 A1 | 3/2007 |

OTHER PUBLICATIONS

Stephen I. Klink et al., "Near-Infrared and Visible Luminescence from Terphenyl-Based Lanthanide(III) Complexes Bearing Amido and Sulfonamido Pendant Arms," Eur. J. Org. Chem. 2000, pp. 1923-1931.

*Primary Examiner* — Johann R Richter
*Assistant Examiner* — Jennifer C Sawyer
(74) *Attorney, Agent, or Firm* — Knobbe, Martens, Olson & Bear LLP

(57) ABSTRACT

A bis(formylphenyl) compound expressed by general formula (2) is useful as a photo-sensitive resist material:

General formula (2)

$$R_4OOCR_3O \underset{(R_2)_m}{\underset{|}{\diagup}} \overset{CHX_2}{\diagdown} R_5 \left[ \underset{(R_1)_n}{\underset{|}{\diagup}} \overset{OR_3COOR_4}{\diagdown} R_6 \right]_k \underset{(R_2)_m}{\underset{|}{\diagup}} \overset{CHX_2}{\diagdown} OR_3COOR_4$$

5 Claims, No Drawings

BIS(FORMYLPHENYL) COMPOUND AND NOVEL POLYNUCLEAR POLYPHENOL COMPOUND DERIVED FROM THE SAME

CROSS-REFERENCE TO RELATED APPLICATIONS

This application is a continuation of U.S. patent application Ser. No. 12/745,367, filed Sep. 20, 2010, now abandoned, which is the U.S. National Phase under 35 U.S.C. §371 of International Application PCT/JP2008/070324, filed Nov. 7, 2008, which claims priority to Japanese Patent Application No. 2007-306710, filed Nov. 28, 2007, and Japanese Patent Application No. 2008-118798, filed Apr. 30, 2008. The International Application was not published under PCT Article 21(2) in English. The disclosure of the U.S. Patent Application is herein incorporated by reference in its entirety.

TECHNICAL FIELD

The present invention relates to a novel bis(formylphenyl) compound and a novel polynuclear polyphenol compound derived therefrom, and more specifically to a novel bis(formylphenyl) compound having at the center of its molecular skeleton a benzene skeleton substituted by an ether group containing an ester group or a carboxyl group, and also having a formylphenyl group similarly substituted by an ether group at both ends of the molecule, as well as a polynuclear polyphenol compound comprising formyl groups of such bis(formylphenyl) compound being further substituted by two hydroxyphenyl groups each.

BACKGROUND ART

Several bis(formylphenyl) compounds have been know where a phenolic hydroxyl group in the molecular structure is protected by an acid-dissociable dissolution suppressing group. For example, Literature 1 describes a bis(formylphenyl) where three phenolic hydroxyl groups are each bonded via single bond with a phenyl ring substituted by an alkoxy-carbonylmethyl group.

Also, Literature 2 describes a bis(formylphenyl) compound comprising phenolic hydroxyl groups of methylene bis(salicylaldehyde) each substituted by an alkoxycarbonyl-methyl group.

In addition, there are polynuclear polyphenol compounds having their phenolic hydroxyl group protected by an acid-dissociable dissolution suppressing group, wherein the phenolic hydroxyl group of such each polynuclear polyphenol compound comprising formyl groups of a bis(formylphenyl) compound each bonded with two hydroxyphenyl groups. For example, Literature 3 describes a polynuclear polyphenol compound whose hydroxyl groups are randomly substituted by acid-dissociable dissolution suppressing groups by approx. 25 to 40 mol %. Also, Literature 4 describes a polynuclear polyphenol compound whose two hydroxyl groups in the bis(hydroxyphenyl) base skeleton are substituted by acid-dissociable dissolution suppressing groups.

In certain fields, however, such as the field of photo-sensitive resist materials, for example, there have been calls in recent years for improvement of resist resolution, heat resistance and contrast, especially the alkali solubility or alkali solution speed in an alkali developing agent of the portions where dissolution suppressing groups have been eliminated, and improvements are expected in bis(formylphenyl) compounds and polynuclear polyphenol compounds that are used as materials for traditionally known polynuclear phenol compounds based on substitution by acid-dissociable dissolution suppressing groups.

Patent Literature

[Non-Patent Literature 1] European Journal of Organic Chemistry, 2000, 1923-1931

[Patent Literature 2] Japanese Patent Laid-open No. 2007-39381

[Patent Literature 3] Japanese Patent Laid-open No. 2006-267996

[Patent Literature 4] International Patent Laid-open No. WO2007-034719

SUMMARY OF THE INVENTION

Problems to be Solved by the Invention

The present invention was developed in light of the aforementioned condition surrounding traditional polynuclear polyphenol compounds whose hydroxyl groups are substituted by acid-dissociable dissolution suppressing groups, and one object of the present invention is to provide a novel polynuclear polyphenol compound offering excellent heat resistance and solubility in solvents, etc., and if such polynuclear polyphenol compound is used as a photo-sensitive resist, for example, through introduction of acid-dissociable dissolution suppressing groups, the resulting photo-sensitive resist will offer excellent alkali solubility or alkali solution speed after elimination of dissolution suppressing groups by means of exposure, etc. In addition, another object of the present invention is to provide a novel bis(formylphenyl) compound which is also useful as an intermediate material for the aforementioned polynuclear polyphenol compound.

Means for Solving the Problems

The inventors examined in earnest, in connection with a polynuclear polyphenol compound that would achieve the aforementioned objects, ways to improve alkali solubility, alkali solution speed and heat resistance of such polynuclear polyphenol compound, especially when it is used as a photo-sensitive resist material, and consequently discovered a novel polynuclear polyphenol compound as well as a novel bis(formylphenyl) compound that can be used as an intermediate material for such polynuclear polyphenol compound, and thereby completed the present invention, wherein such polynuclear polyphenol compound has at least three benzene skeletons at the center of its molecular skeleton where a phenolic hydroxyl group is substituted by an ether group containing an ester group or a carboxyl group; has two phenol groups each at both ends of the molecule, each having at least one phenolic hydroxyl group; and wherein the ether group is a single-ring or condensed-ring aromatic hydrocarbon group, or aliphatic saturated hydrocarbon carboxyl group or alkylester group that may have a single-ring or condensed-ring aromatic hydrocarbon group.

In other words, a novel bis(formylphenyl) compound proposed by the present invention is expressed by general formula (1) below:

General formula (1)

[Chemical 1]

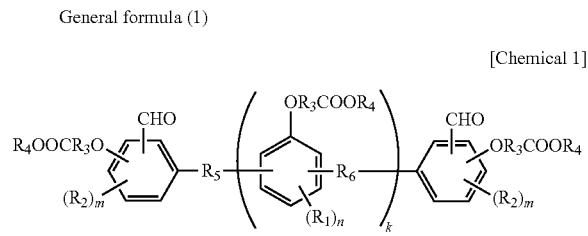

In the formula, $R_1$ and $R_2$ each independently represent an alkyl group with 1 to 8 carbon atoms or alkoxyl group with 1 to 8 carbon atoms, $R_3$ is a single-ring or condensed-ring aromatic hydrocarbon group with 6 to 15 carbon atoms or aliphatic saturated hydrocarbon group with 1 to 8 carbon atoms that may have a single-ring or condensed-ring aromatic hydrocarbon group with 6 to 15 carbon atoms, $R_4$ is a hydrogen atom or alkyl group with 1 to 6 carbon atoms, $R_5$ and $R_6$ may be the same or different and each represent a bivalent aliphatic saturated hydrocarbon group with 1 to 8 carbon atoms, m is an integer of 0 or 1 to 3, n is an integer of 0 or 1 to 3, and k is an integer of 1 to 3, but if k is 2 or greater, then $R_6$, $R_1$ and n in each phenyl group may all be the same or different.

Another novel polynuclear polyphenol compound proposed by the present invention is expressed by general formula (2) below:

General formula (2)

[Chemical 2]

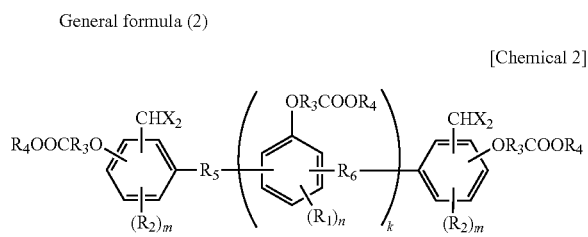

In the formula, $R_1$, $R_2$, $R_3$, $R_5$, $R_6$, k, m and n are the same as the corresponding items in general formula (1), respectively, $R_4$ is a hydrogen atom or primary alkyl group or secondary alkyl group with 1 to 6 carbon atoms, and X is a hydroxyphenyl group expressed by general formula (3) below:

General formula (3)

[Chemical 3]

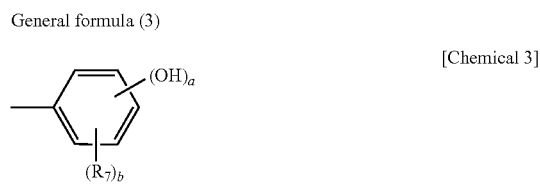

In the formula, $R_7$ is an alkyl group with 1 to 8 carbon atoms or alkoxyl group with 1 to 8 carbon atoms, a is an integer of 1 to 3, b is an integer of 0 to 4, where $1 \leq a+b \leq 5$, and if b is 2 or greater, then $R_7$'s may be the same or different.

In addition, a polynuclear polyphenol compound whose hydroxyphenyl group per general formula (3) above is expressed by general formula (4) below is a favorable embodiment of a polynuclear polyphenol compound proposed by the present invention:

General formula (4)

[Chemical 4]

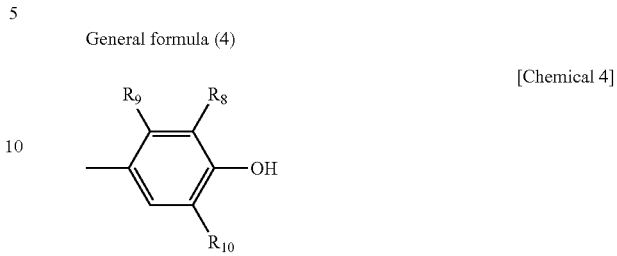

In the formula, $R_8$, $R_9$ and $R_{10}$ each independently represent a hydrogen atom or alkyl group with 1 to 8 carbon atoms or alkoxyl group with 1 to 8 carbon atoms.

Effects of the Invention

A novel bis(formylphenyl) compound conforming to the present invention offers excellent heat resistance represented by high glass transition temperature, etc., and also offers excellent reactivity because it has highly reactive formyl groups in the phenyl cores at both ends as well as similarly reactive terminal ester groups or carboxyl groups, and can therefore be used favorably as an intermediate material for various types of polynuclear polyphenol compounds obtained by reaction with phenols, photo-sensitive resist, material or modifier for phenol resins and epoxy resins, or color developing material for thermo-sensitive recording materials, among others.

Another novel polynuclear polyphenol proposed by the present invention has the aforementioned bis(formylphenyl) as its center skeleton, which is further bonded by four hydroxyphenyl groups, and therefore it offers excellent heat resistance represented by high glass transition temperature, etc., and because this polynuclear polyphenol also offers excellent alkali solubility and alkali solution speed, it is useful as a photo-sensitive resist material and can also be used favorably as a material or modifier for phenol resins and epoxy resins.

BEST MODE FOR CARRYING OUT THE INVENTION

A novel bis(formylphenyl) compound proposed by the present invention is expressed by general formula (1) above.

In the formula, $R_1$ and $R_2$ each independently represent an alkyl group with 1 to 8 carbon atoms or alkoxyl group with 1 to 8 carbon atoms, $R_3$ is a single-ring or condensed-ring aromatic hydrocarbon group with 6 to 15 carbon atoms or aliphatic saturated hydrocarbon group with 1 to 8 carbon atoms that may have a single-ring or condensed-ring aromatic hydrocarbon group with 6 to 15 carbon atoms, $R_4$ is a hydrogen atom or alkyl group with 1 to 6 carbon atoms, $R_5$ and $R_6$ may be the same or different and each represent a bivalent aliphatic saturated hydrocarbon group with 1 to 8 carbon atoms, m is an integer of 0 or 1 to 3, n is an integer of 0 or 1 to 3, and k is an integer of 1 to 3, but if k is 2 or greater, then $R_6$, $R_1$ and n in each phenyl group may all be the same or different.

As for $R_1$ and $R_2$, specific examples of an alkyl group with 1 to 8 carbon atoms include methyl group, ethyl group, propyl group, isopropyl group, butyl group, sec-butyl group, t-butyl group, pentyl group, 3-methylpentyl group, cyclopropyl group, cyclopentyl group, 3-metylcyclopentyl group, cyclohexyl group, 2,4-dimethylcyclohexyl group, cycloheptyl group and other straight-chain, branched-chain or cyclic saturated hydrocarbon groups. Examples of an alkoxyl group with 1 to 8 carbon atoms include methoxy group, ethoxy group, propoxy group, isopropoxy group, butoxy group, t-butoxy group, pentyloxy group, 3-methylpentyloxy group, cyclopropyloxy group, cyclopentyloxy group, 3-methylcyclopentyloxy group, cyclohexyloxy group, 2,4-dimethylcyclohexyloxy group, cycloheptyloxy group and other straight-chain, branched-chain or cyclic saturated hydrocarbon alkoxyl groups. Among the above, an alkyl group with 1 to 4 carbon atoms or alkoxyl group with 1 to 4 carbon atoms is desirable, where an alkyl group with 1 or 2 carbon atoms is more desirable.

While m is an integer of 0 or 1 to 3, desirably 0 or 1 or 2, n is an integer of 0 or 1 to 3, desirably 1 or 2.

As for $R_1$, the bonding position to the phenyl core may be any of the o-position, m-position and p-position as long as bonding is possible, but substitution in one of the o-position and p-position relative to the ether group bonding with the phenyl core is preferred because it makes industrial production easier.

Also in general formula (1), $R_5$ and $R_6$ may be the same or different and each represent a bivalent aliphatic saturated hydrocarbon group with 1 to 8 carbon atoms, where the number of carbon atoms are desirably 1 to 6, or more desirably 1 to 3. Specific examples include methylene, 1,1-ethylidene, 1,1-propylidene, 2,2-propylidene and other alkylidene groups, 1,2-ethylene, 1,2-propylene, 1,3-propylene and other alkylene groups.

As for the substitution positions of $R_5$ and $R_6$ in the phenyl core, the o-position or p-position relative to the ether group is preferred because it allows for synthesis with a higher yield. The same applies to the substitution positions when k is 2 or 3, As for the substitution position of the formyl group, the o-position or p-position relative to the ether group is preferred.

Also in general formula (1), $R_3$ is a single-ring or condensed-ring aromatic hydrocarbon group with 6 to 15 carbon atoms or aliphatic saturated hydrocarbon group with 1 to 8 carbon atoms that may have a single-ring or condensed-ring aromatic hydrocarbon group with 6 to 15 carbon atoms, while $R_4$ is a hydrogen atom or alkyl group with 1 to 6 carbon atoms.

If $R_3$ is a single-ring or condensed-ring aromatic hydrocarbon group with 6 to 15 carbon atoms, the single-ring or condensed-ring aromatic hydrocarbon group may be substituted by an alkyl group, where specific examples include p-phenylene, m-phenylene, o-phenylene, 2-methyl-1,4-phenylene, 2,6-dimethyl-1,4-phenylene, 2-propyl-1,4-phenylene and other single-ring aromatic hydrocarbon groups, 1,5-naphthylene, 2,7-naphthyleneanthracene-2,7-diyl, fluorene-2,7-diyl and other condensed-ring aromatic hydrocarbon groups. Among others, a single-ring aromatic hydrocarbon group is preferred.

If $R_3$ is an aliphatic saturated hydrocarbon group with 1 to 8 carbon atoms that may have a single-ring or condensed-ring aromatic hydrocarbon group with 6 to 15 carbon atoms, then one embodiment being a bivalent aliphatic saturated hydrocarbon group with 1 to 8 carbon atoms that has no aromatic hydrocarbon group is a straight-chain or branched-chain alkylene group or alkylidene group with 1 to 8 carbon atoms, where specific examples include methylene, ethylene, 1,3-propylene, 1,1-propylidene, 1,4-butylene, 2-methyl-1,3-propylene, hexamethylene, 1,1,2,2-tetramethylethylene, 1,1-ethylidene, 2,4-butylene, 1,1-n-hexylidene and other straight-chain or branched-chain alkylene groups or alkylidene groups.

Among others, an alkylene group or alkylidene group with 1 to 4 carbon atoms is preferred.

In addition, if $R_3$ is an aliphatic saturated hydrocarbon group with 1 to 8 carbon atoms that may have a single-ring or condensed-ring aromatic hydrocarbon group with 6 to 15 carbon atoms, then another embodiment being an aliphatic saturated hydrocarbon group having an aromatic hydrocarbon group is preferably an aliphatic hydrocarbon group with 1 to 8 carbon atoms where the main chain has a single-ring or condensed-ring aromatic hydrocarbon group, as expressed by general formula (5) below:

$$—(R_{11})c-(R_{12})d-(R_{13})e-$$ 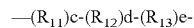 General formula (5)

In the formula, $R_{11}$ and $R_{13}$ each independently represent an aliphatic saturated hydrocarbon with 1 to 8 carbon atoms, c and e are 1 or 0, and d is 1, where the total number of carbon atoms of $R_{11}+R_{13}$ is 1 to 8, c and e are not both 0 at the same time, and $R_{12}$ is a single-ring or condensed-ring aromatic hydrocarbon group with 6 to 15 carbon atoms. The single-ring or condensed-ring aromatic hydrocarbon group with 6 to 15 carbon atoms expressed by $R_{12}$ is the same as the single-ring or condensed-ring aromatic hydrocarbon group that applies when $R_3$ is a single-ring or condensed-ring aromatic hydrocarbon group with 6 to 15 carbon atoms.

Accordingly, specific examples of this aliphatic hydrocarbon group with 1 to 8 carbon atoms having a single-ring or condensed-ring aromatic hydrocarbon group with 6 to 15 carbon atoms include the following, among others:

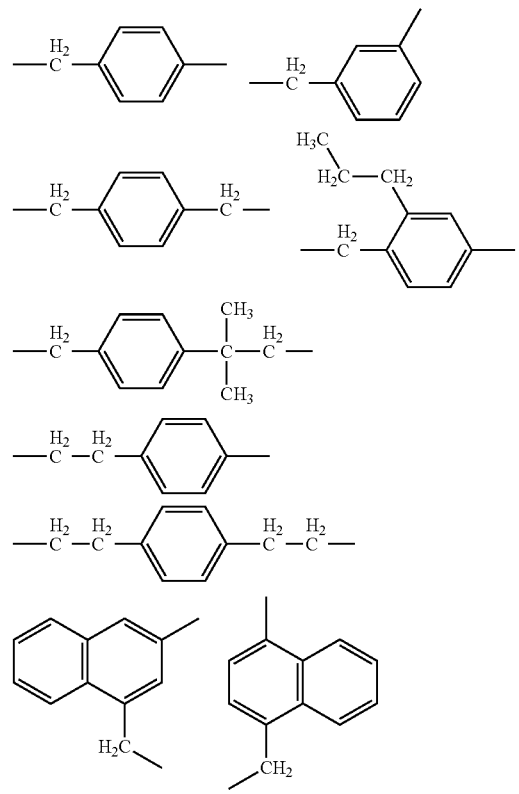

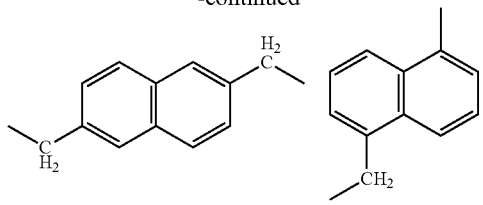

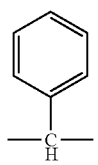

In addition, $R_3$ in general formula (1), or $R_{11}$ when $R_3$ is expressed by general formula (5), is preferably a primary or secondary carbon atom because a carbon atom bonded with a phenyloxy group is stable in the presence of acid.

Furthermore, $R_4$ is a hydrogen atom or alkyl group with 1 to 6 carbon atoms, where the alkyl group with 1 to 6 carbon atoms is a straight-chain, branched-chain or cyclic alkyl group, specific examples of which include methyl, ethyl, n-butyl, t-butyl, sec-butyl, isopropyl, n-propyl and cyclohexyl, etc. Among others, a straight-chain or branched-chain alkyl group with 1 to 4 carbon atoms is preferred.

Accordingly, specific examples of an ester substituted hydrocarbon group bonding with a phenyloxy group in the bis(formylphenyl) compound expressed by general formula (1), or specifically carboxy hydrocarbon group or alkoxycarbonyl hydrocarbon group represented by —$R_3COOR_4$, include carboxymethyl group, methoxycarbonylmethyl group, carboxypropyl group, ethoxycarbonylpropyl group, 3-methoxycarbonyl-2-methyl-1-propyl group and methoxycarbonylpropyl group, or the following, among others:

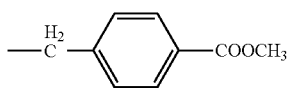

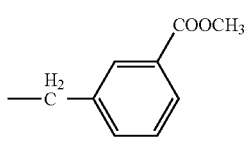

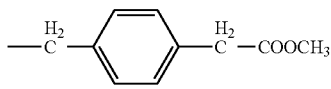

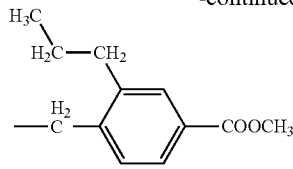

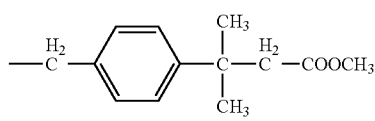

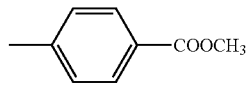

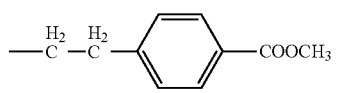

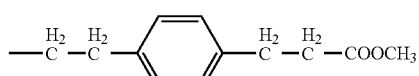

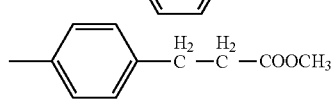

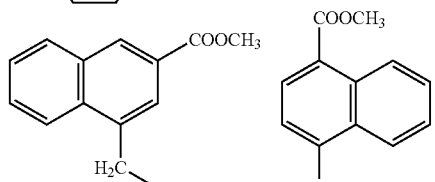

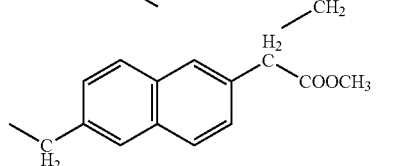

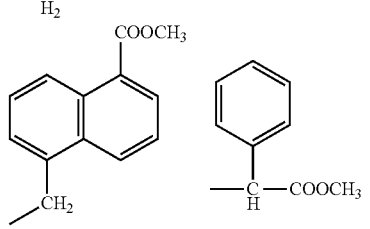

Accordingly, a bis(formylphenyl) compound expressed by general formula (1), as proposed by the present invention, is preferably one expressed by general formula (6) or general formula (7) below:

General formula (6)

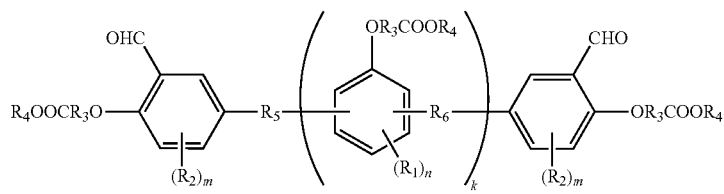

(In the formula, $R_1$ to $R_6$, k, m and n are the same as the corresponding items in general formula (1), respectively.)

General formula (7)

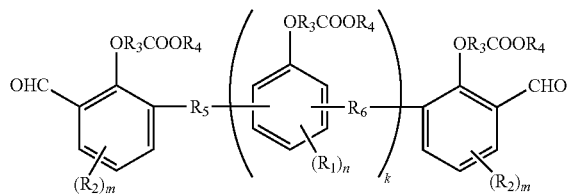

(In the formula, $R_1$ to $R_6$, k, m and n are the same as the corresponding items in general formula (1), respectively.)

Specific examples of a compound expressed by general formula (6) or (7) above include the following when k is 1:

2,6-bis{(3-formyl-4-methoxycarbonylmethoxyphenyl)methyl}-4-methyl-1-methoxycarbonylmethoxybenzene

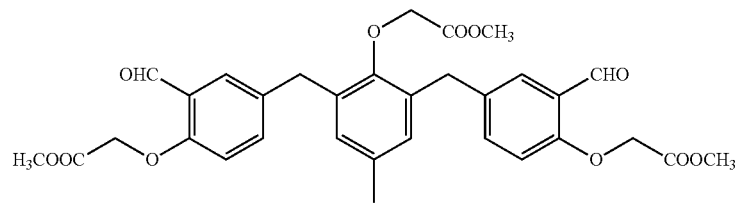

2,6-bis{(3-formyl-2,5-dimethyl-4-methoxycarbonylmethoxyphenyl)methyl}-4-methyl-1-methoxycarbonylmethoxybenzene

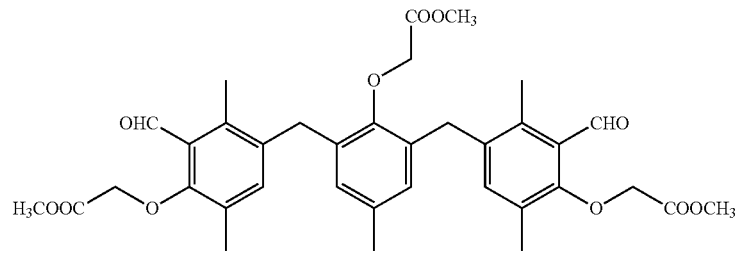

Examples of such compound when k is 2 include the following:

Bis{3-(3-formyl-4-methoxycarbonylmethoxyphenyl)methyl-2,5-dimethyl-4-methoxycarbonylmethoxyphenyl}methane

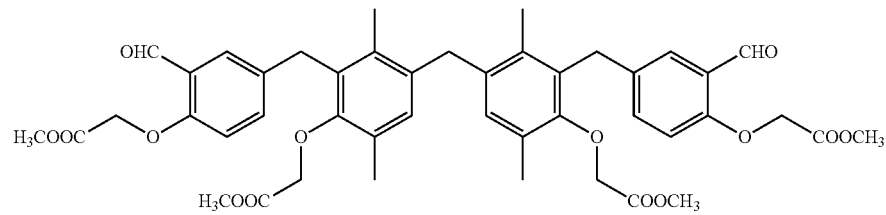

Other examples include the following, among others:
2,6-bis{(3-formyl-4-methoxycarbonylmethoxyphenyl)methyl}-4-t-butyl-1-methoxycarbonylmethoxybenzene,
2,6-bis{(3-formyl-5-cyclohexyl-4-methoxycarbonylmethoxyphenyl)methyl}-4-methyl-1-methoxycarbonylmethoxybenzene,
2,4-bis{(3-formyl-4-methoxycarbonylmethoxyphenyl)methyl}-6-methyl-1-methoxycarbonylmethoxybenzene,
2,6-bis{(5-formyl-2-methoxycarbonylmethoxyphenyl)methyl}-4-methyl-1-methoxycarbonylmethoxybenzene,
2,6-bis{1-(3-formyl-4-methoxycarbonylmethoxyphenyl)ethyl}-4-methyl-1-methoxycarbonylmethoxybenzene,
2,6-bis{1-methyl-1-(3-formyl-4-methoxycarbonylmethoxyphenyl)ethyl}-4-methyl-1-methoxycarbonylmethoxybenzene,
2,6-bis{(3-formyl-4-(4-methoxycarbonylphenyl)methoxyphenyl)methyl}-4-methyl-1-(4-methoxycarbonylphenyl)methoxybenzene,
2,6-bis{(3-formyl-4-(4-carboxyphenyl)methoxyphenyl)methyl}-4-methyl-1-(4-carboxyphenyl)methoxybenzene,
2,6-bis{(3-formyl-4-carboxymethoxyphenyl)methyl}-4-methyl-1-carboxymethoxybenzene,
2,6-bis{(3-formyl-4-methoxycarbonylmethoxyphenyl)methyl}-4-methoxy-1-methoxycarbonylmethoxybenzene,
2,6-bis{(3-formyl-5-methoxy-4-methoxycarbonylmethoxyphenyl)methyl}-4-methyl-1-methoxycarbonylmethoxybenzene,
Bis{3-(3-formyl-5-methyl-4-methoxycarbonylmethoxyphenyl)methyl-5-methyl-2-methoxycarbonylmethoxyphenyl}methane, and
Bis{3-(3-formyl-4-carboxymethoxyphenyl)methyl-2,5-dimethyl-4-carboxymethoxyphenyl}methane.

The manufacturing method of any such bis(formylphenyl) compound expressed by general formula (1) above, as proposed by the present invention, is not specifically limited and, for example, a bis(hydroxy-formylphenyl) compound expressed by general formula (8) below may be used as the direct material to be reacted with a halogenated alkoxycarbonyl hydrocarbon expressed by general formula (9) below, according to a known phenylether manufacturing method in the presence of a base, as shown by reaction formula (1) below.

General formula (8)

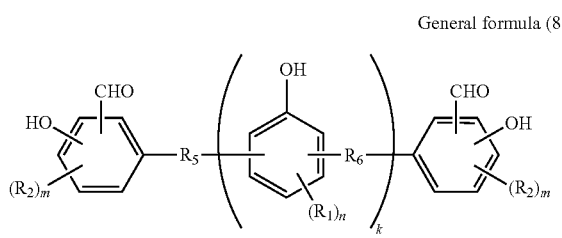

In the formula, $R_1$, $R_2$, n, m, k, $R_5$ and $R_6$ are the same as the corresponding items in general formula (1), respectively.

$$Z—R_3COOR_4 \qquad \text{General formula (9)}$$

In the formula, Z is a halogen atom, $R_3$ is the same as the corresponding item in general formula (1), and $R_4$ is an alkyl group with 1 to 6 carbon atoms. The halogen atom is preferably a chlorine atom or bromine atom.

Reaction formula (1)

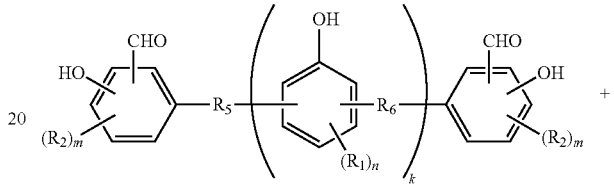

(k + 2)  (Z—$R_3COOR_4$) ⟶

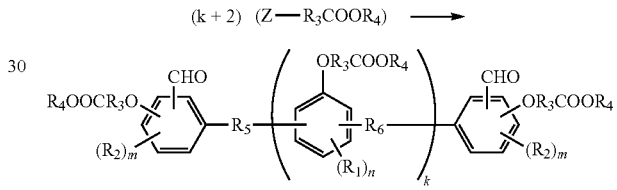

The method of manufacturing a bis(formylphenyl) compound expressed by general formula (1) above, as proposed by the present invention, by using a bis(hydroxy-formylphenyl) expressed by general formula (8) above as the direct material and causing it to react with a halogenated alkoxycarbonyl hydrocarbon expressed by general formula (9) above in the presence of a base, as shown by reaction formula (1) above, is explained more specifically.

For example, reaction formula (2) below applies when 2,6-bis{(3-formyl-4-hydroxyphenyl)methyl}-4-methylphenol is used as the direct material, while methylesterchloroacetate is used as the halogenated alkoxycarbonyl hydrocarbon, to obtain 2,6-bis{(3-formyl-4-methoxycarbonylmethoxyphenyl)methyl}-4-methyl-1-methoxycarbonylmethoxybenzene:

Reaction formula (2)

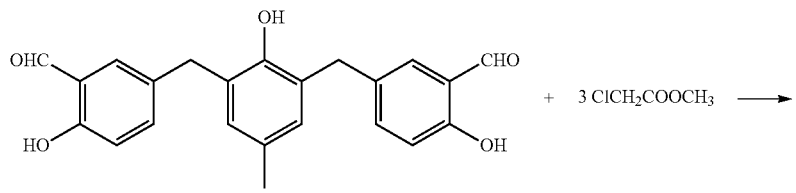

-continued

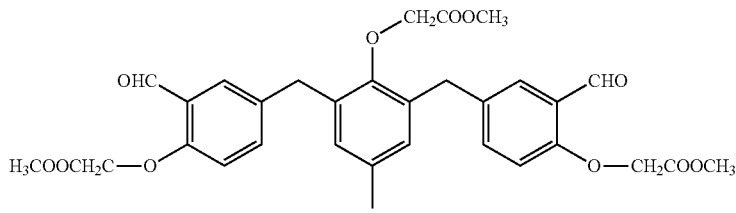

In the manufacturing method illustrated in the example of reaction formula (2), a bis(hydroxy-formylphenyl) compound is reacted with a halogenated alkoxycarbonyl hydrocarbon in a reaction solvent such as dimethylformaldehyde in the presence of a base such as potassium carbonate.

Either an organic base or inorganic base can be used, but preferable examples of organic base include tetramethylammonium hydroxide or other hydroxy quaternary amine, or 1,8-diazabicyclo[5.4.0]undec-7-ene (abbreviated as "DBU"), among others.

Preferable examples of inorganic base include, among others, sodium hydroxide, potassium hydroxide and other alkali metal hydroxides, potassium carbonate, sodium carbonate and other alkali metal carbonate salts, sodium hydride, potassium hydride, lithium hydride and other alkali metal hydrides, and t-butoxy potassium and other alkoxyalkali metals.

Any such base is added by an amount normally in a range of (2+k) mol to 1.5×(2+k) mol, or preferably in a range of 1.15×(2+k) mol to 1.35×(2+k) mol, per 1 mol of the bis (hydroxy-formylphenyl) compound expressed by general formula (8). Here, k represents the value of k in general formula (8) above.

Preferable examples of the solvent used in the reaction include, among others, dioxane, THF and other ethers, dimethylformamide, dimethylacetamide and other amides, dimethylsulfoxide, hexamethylenephosphonic acid amide, pyridine, 4-methylpyridine, N-methylpyrrolidone and other amines, or any mixture thereof.

The amount of solvent used is normally in a range of 1 to 10 parts by weight, or preferably in a range of 2 to 5 parts by weight, per 1 part by weight of the material bis(hydroxy-formylphenyl) compound, from the viewpoint of reaction volume ratio, etc.

If necessary, potassium iodide or other alkali metal iodide, copper, copper chloride or other copper compound, or phase transfer catalyst or other reaction promoting additive may be added to promote the etherification reaction.

Although the method or sequence to introduce the reaction materials at the time of reaction is not limited, normally the method to mix a bis(hydroxy-formylphenyl) compound expressed by general formula (8) with a base to produce an oxy salt, and then add to a solution of this mixture a halogenated alkoxycarbonyl hydrocarbon expressed by general formula (9), is preferable due to a better yield.

The reaction is carried out for several hours, such as 2 to 20 hours, at a temperature normally in a range of 20 to 150° C., or preferably in a range of 50 to 80° C. The reaction pressure is normally in a range of slight decompression to slight compression, or preferably at a normal pressure or so.

After the reaction, an appropriate amount of toluene, cyclohexane or other organic solvent is added, with water, to the reaction mixture to wash and separate the organic layer, and (if necessary, the organic layer is washed with an aqueous acid solution and neutralized) the solvent is distilled and removed from the organic layer, after which the residue is mixed with methanol or other aliphatic lower alcohol, or if necessary, toluene or other aromatic hydrocarbon or methylethylketone or other aliphatic ketone, to crystallize or otherwise distill and remove the aforementioned washing solvent, in order to obtain the target substance, or specifically a bis (formylphenyl) compound expressed by general formula (1).

Also with respect to any bis(formylphenyl) compound expressed by general formula (1) where $R_4$ is a hydrogen atom, the manufacturing method to obtain such compound whose ether group is a carboxy hydrocarbon oxy substitution product is not specifically limited. For example, however, the alkoxycarbonyl hydrocarbon group (—$R_3COOR_4$) substitution product in the bis(formylphenyl) compound obtained as above, where $R_4$ is a primary or secondary alkyl group, can be hydrolyzed in the presence of an alkali without using any solvent or in a solvent, to obtain a carboxy hydrocarbon group (—$R_3COOH$) substitution product with ease.

For example, if 2,6-bis{(3-formyl-4-methoxycarbonyl-methoxyphenyl)methyl}-4-methyl-1-methoxycarbonyl-methoxybenzene obtained according to reaction formula (2) above is hydrolyzed in the presence of an alkali without using any solvent or in a solvent, 2,6-bis{(3-formyl-4-carboxymethoxyphenyl)methyl}-4-methyl-1-carboxymethoxy-benzene can be obtained, as shown by reaction formula (3) below:

Reaction formula (3)

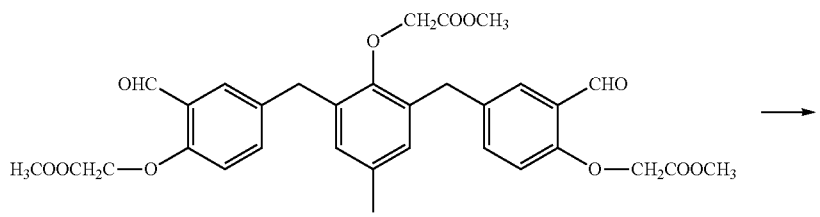

-continued

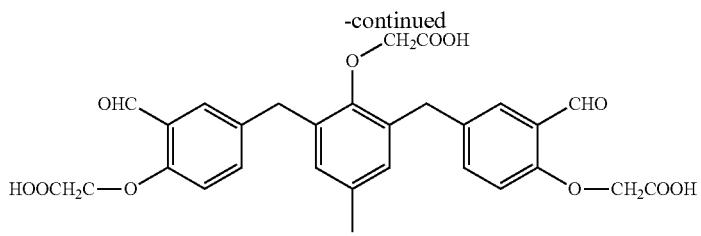

In the manufacturing method of a bis(formylphenyl) compound where $R_4$ is a hydrogen atom as illustrated in the example of reaction formula (3) above, it is desirable that $R_4$ in the alkoxycarbonyl hydrocarbon group (—$R_3COOR_4$) of the bis(formylphenyl) compound be a primary alkyl group if $R_4$ in general formula (1) is an alkyl group, as is the case with any known hydrolysis reaction of ester group, because it facilitates the hydrolysis reaction.

Accordingly, a carboxy hydrocarbon substitution product where $R_4$ is a hydrogen atom per general formula (1) can be obtained easily by hydrolyzing such bis(formylphenyl) compound using an aqueous alkali solution of sodium hydroxide, tetramethylammonium hydroxide, etc.

As for the aqueous alkali solution used in the hydrolysis reaction, an inorganic aqueous solution of strong alkali such as sodium hydroxide, potassium hydroxide, etc., or organic aqueous solution of strong alkali such as tetramethylammonium hydroxide, etc., is preferable, where the alkali concentration of such solution is in a range of 5 to 50%, or preferably in a range of 10 to 30%. The amount of alkali used is normally in a range of 2 to 6 mol, or preferably in a range of 2 to 4 mol, per 1 mol of the material bis(formylphenyl) compound. The reaction temperature is normally in a range of 0 to 100° C., or preferably in a range of 20 to 60° C. Under these reaction conditions, reaction normally ends in around 0.5 to 10 hours.

After the reaction, a solvent that separates from water is added to wash the obtained product and remove the oil layer, if necessary. Thereafter, a solvent that separates from water is added, together with an acid, to neutralize the aqueous alkali solution and target alkali salt, and then the water layer is removed and the reaction product is refined from the obtained oil layer according to any known method as mentioned above, and if necessary, a product of higher purity can also be obtained.

In addition, the direct material, or specifically a bis(hydroxy-formylphenyl) compound expressed by general formula (8) above, can be obtained easily by causing a bis (hydroxyphenyl) compound corresponding to a direct material bis(hydroxy-formylphenyl) compound that in turn corresponds to the target bis(formylphenyl) compound, to react with hexamethylenetetramine in the presence of trifluoroacetate or other acid, according to reaction formula (4) below, followed by a hydrolysis of the reaction product, or by methylolating a bis(hydroxyphenyl) compound and then causing the resulting product with hexamethylenetetramine in the presence of trifluoroacetate or other acid, according to reaction formula (5) below, followed by a hydrolysis of the reaction product.

As shown in reaction formula (6) below, it can also be obtained by reacting di(hydroxymethyl)phenol and hydroxybenzaldehyde in the presence of phosphate, trifluoroacetate or other acid catalyst.

Note that in the formula, $R_1$ and $R_2$ each independently represent an alkyl group with 1 to 8 carbon atoms or alkoxyl group with 1 to 8 carbon atoms, $R_5$ and $R_6$ may be the same or different and each represent a bivalent aliphatic saturated hydrocarbon group with 1 to 8 carbon atoms, m is an integer of 0 or 1 to 3, n is an integer of 0 or 1 to 3, and k is an integer of 1 to 3, but if k is 2 or greater, then $R_6$, $R_1$ and n in each phenyl group may all be the same or different.

Reaction formula (4)

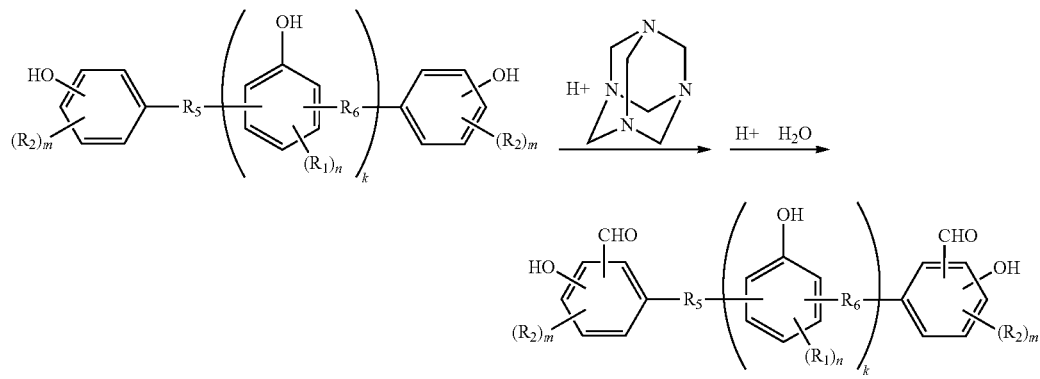

Reaction formula (5)

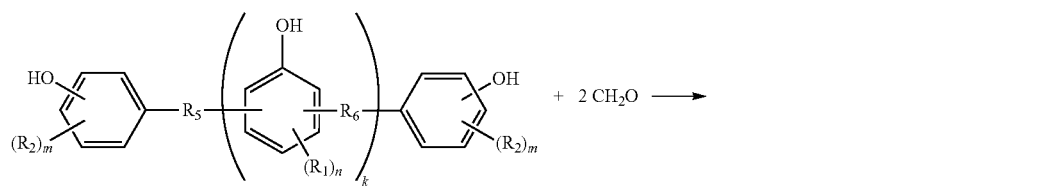

-continued

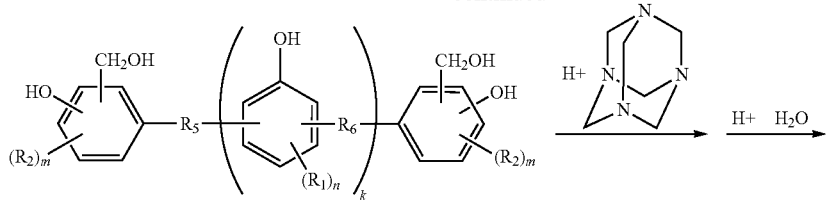

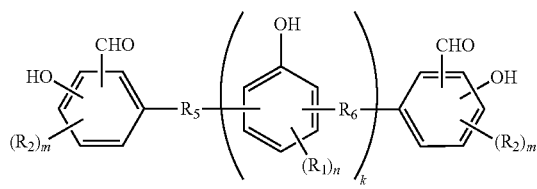

Reaction formula (6)

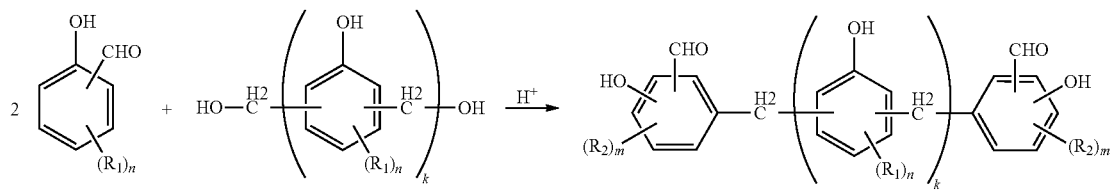

Examples of such bis(hydroxy-formylphenyl) compound expressed by general formula (8) include the following, among others:

2,6-bis{(3-formyl-4-hydroxyphenyl)methyl}-4-methyl-1-hydroxybenzene

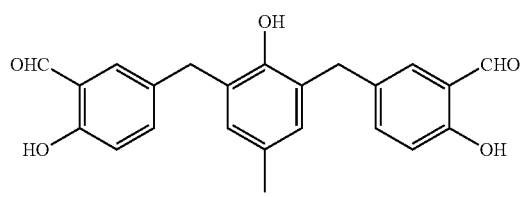 [SMILES: Cc1cc(Cc2ccc(O)c(C=O)c2)c(O)c(Cc2ccc(O)c(C=O)c2)c1]

2,6-bis{(3-formyl-2,5-dimethyl-4-hydroxyphenyl)methyl}-4-methyl-1-hydroxybenzene

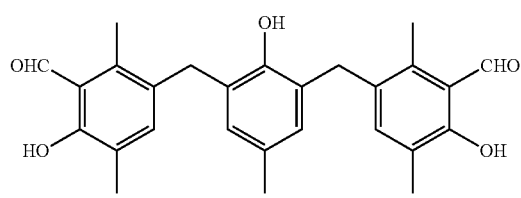 [SMILES: Cc1cc(Cc2cc(C)c(O)c(C=O)c2C)c(O)c(Cc2cc(C)c(O)c(C=O)c2C)c1]

Other examples include the following, among others:
2,6-bis{(3-formyl-4-hydroxyphenyl)methyl}-4-t-butyl-1-hydroxybenzene,
2,6-bis{(3-formyl-5-cyclohexyl-4-hydroxyphenyl)methyl}-4-methyl-1-hydroxybenzene,
2,4-bis{(3-formyl-4-hydroxyphenyl)methyl}-6-methyl-1-hydroxybenzene,
2,6-bis{(5-formyl-2-hydroxyphenyl)methyl}-4-methyl-1-hydroxybenzene,
2,6-bis{1-(3-formyl-4-hydroxyphenyl)ethyl}-4-methyl-1-hydroxybenzene,
2,6-bis{1-methyl-1-(3-formyl-4-hydroxyphenypethyl}-4-methyl-1-hydroxybenzene,
2,6-bis[(3-formyl-4-hydroxyphenyl)methyl]-4-ethyl-1-hydroxybenzene,
2,6-bis[(3-formyl-4-hydroxyphenyl)methyl]-4-isopropyl-1-hydroxybenzene,
2,6-bis[(3-formyl-4-hydroxyphenyl)methyl]-4-n-butyl-1-hydroxybenzene,
2,6-bis[(3-formyl-4-hydroxyphenyl)methyl]-4-n-propyl-1-hydroxybenzene,
2,6-bis[(5-formyl-2-hydroxyphenyl)methyl]-4-ethyl-1-hydroxybenzene,
2,6-bis[(3-formyl-4-hydroxyphenyl)methyl]-4-cyclopentyl-1-hydroxybenzene,
2,6-bis[(2-formyl-4-hydroxyphenyl)methyl]-4-cyclopentyl-1-hydroxybenzene,
2,6-bis[(3-formyl-4-hydroxyphenyl)methyl]-4-cyclohexyl-1-hydroxybenzene,
2,6-bis[(3-formyl-2-hydroxyphenyl)methyl]-4-cyclohexyl-1-hydroxybenzene,
2,6-bis[(2-formyl-4-hydroxyphenyl)methyl]-4-cyclohexyl-1-hydroxybenzene,
Bis{3-(3-formyl-4-hydroxyphenyl)methyl-2,5-dimethyl-4-hydroxyphenyl}methane, and
Bis{3-(3-formyl-5-methyl-4-hydroxyphenyl)methyl-5-methyl-2-hydroxyphenyl}methane.

Next, another novel compound proposed by the present invention, or specifically a polynuclear polyphenol compound that can be derived from the aforementioned bis(formylphenyl) compound, is expressed by general formula (2) below:

General formula (2)

[Chemical 2]

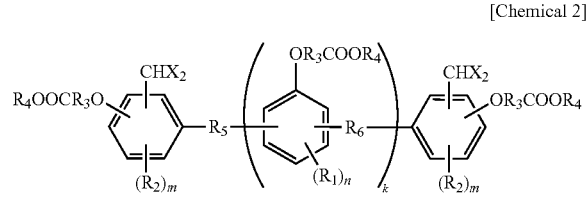

In the formula, $R_1$, $R_2$, $R_3$, $R_5$, $R_6$, k, m and n are the same as the corresponding items in general formula (1), respectively, $R_4$ is a hydrogen atom or primary alkyl group or secondary alkyl group with 1 to 6 carbon atoms, and X is a hydroxyphenyl group expressed by general formula (3) below:

General formula (3)

[Chemical 3]

In the formula, $R_7$ is an alkyl group with 1 to 8 carbon atoms or alkoxyl group with 1 to 8 carbon atoms, a is an integer of 1 to 3, b is an integer of 0 to 4, where $1 \le a+b \le 5$, and if b is 2 or greater, then $R_7$'s may be the same or different.

Regarding the hydroxyphenyl group in general formula (3) above, a preferable hydroxyphenyl group is expressed by general formula (4) below:

General formula (4)

[Chemical 4]

In the formula, $R_8$, $R_9$ and $R_{10}$ each independently represent a hydrogen atom or alkyl group with 1 to 8 carbon atoms or alkoxyl group with 1 to 8 carbon atoms.

In general formula (3) above, $R_7$ is an alkyl group with 1 to 8 carbon atoms or alkoxyl group with 1 to 8 carbon atoms, while in general formula (4) above $R_8$, $R_9$ and $R_{10}$ are each a hydrogen atom or alkyl group with 1 to 8 carbon atoms or alkoxyl group with 1 to 8 carbon atoms, where specific examples of the alkyl group with 1 to 8 carbon atoms or alkoxyl group with 1 to 8 carbon atoms are the same as those of $R_1$ in general formula (1).

In general formula (3), if b=3 or specifically $R_7$ undergoes three substitutions or less, if a=1 or specifically the hydroxyl group undergoes one substitution, and if at least one m-position of the hydroxyl group is not substituted, then a substitution group that can bond with the formyl group at the p-position relative to the hydroxyl group is preferred from the viewpoint of synthesis. If b=4 or specifically $R_7$ undergoes four substitutions, on the other hand, a substitution group that can bond with the formyl group at the o-position relative to the hydroxyl group is preferred from the viewpoint of synthesis.

Accordingly, specific examples of a substituted phenyl group expressed by general formula (3) or (4) above include, among others, those having one hydroxyl group such as 4-hydroxyphenyl group, 3-methyl-4-hydroxyphenyl group, 2-methyl-4-hydroxyphenyl group, 2,5-dimethyl-4-hydroxyphenyl group, 3,5-dimethyl-4-hydroxyphenyl group, 2,3,5-trimethyl-4-hydroxyphenyl group, 3-ethyl-4-hydroxyphenyl group, 3-isopropyl-4-hydroxyphenyl group, 3-t-butyl-4-hydroxyphenyl group, 3-t-butyl-6-methyl-4-hydroxyphenyl group, 3,5-di-t-butyl-4-hydroxyphenyl group, 3-sec-butyl-4-hydroxyphenyl group, 3-t-octyl-4-hydroxyphenyl group, 3-t-butyl-5-methyl-4-hydroxyphenyl group, 3-cyclohexyl-4-hydroxyphenyl group, 2-methyl-5-cyclohexyl-4-hydroxyphenyl group, 5-methyl-2-hydroxyphenyl group, 4,6-dimethyl-2-hydroxyphenyl group, 3,4,6-trimethyl-2-hydroxyphenyl group, 3,5-di-t-butyl-2-hydroxyphenyl group, 5-t-octyl-2-hydroxyphenyl group, 3-methoxy-4-hydroxyphenyl group, 5-methoxy-2-hydroxyphenyl group, 3-n-hexyloxy-4-hydroxyphenyl group, 3-n-octyloxy-4-hydroxyphenyl group, and 5-butoxy-2-hydroxyphenyl group.

Examples where there are two or three hydroxyl groups include, among others, 2,4-dihydroxyphenyl group, 3,4-dihydroxyphenyl group, 2-methyl-4,5-dihydroxyphenyl group, 3-methyl-4,5-dihydroxyphenyl group, 5-methyl-2,4-dihydroxyphenyl group, and 2,3,4-trihydroxyphenyl group.

Accordingly, a preferred form of polynuclear polyphenol compound expressed by general formula (2) is one expressed by general formula (10) or (11) below.

General formula (10)

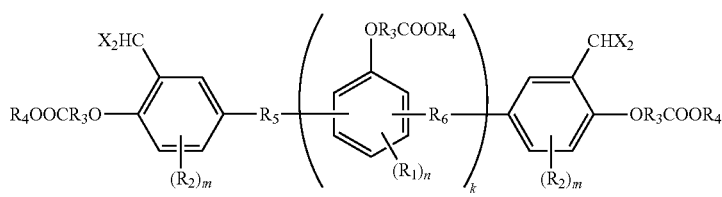

(In the formula, $R_1$ to $R_6$, X, k, m and n are the same as the corresponding items in general formula (2), respectively.)

General formula (11)

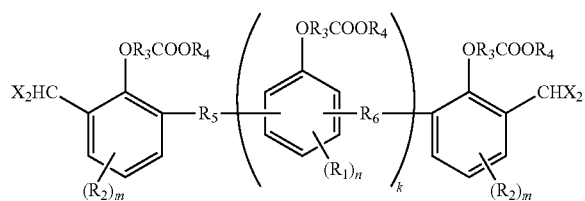

(In the formula, $R_1$ to $R_6$, X, k, m and n are the same as the corresponding items in general formula (2), respectively.)

Specific examples of a polynuclear polyphenol compound expressed by general formula (10) or (11) above include the following when k is 1:

2,6-bis[{3-bis(2,5-dimethyl-4-hydroxyphenyl)methyl-4-carboxymethoxyphenyl}methyl]-4-methyl-1-carboxymethoxybenzene

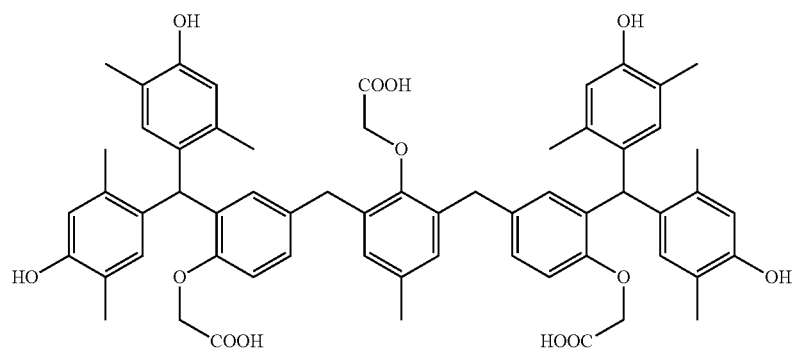 [SMILES: Cc1cc(Cc2ccc(OCC(=O)O)c(C(c3cc(C)c(O)cc3C)c3cc(C)c(O)cc3C)c2)c(OCC(=O)O)c(Cc2ccc(OCC(=O)O)c(C(c3cc(C)c(O)cc3C)c3cc(C)c(O)cc3C)c2)c1]

2,6-bis[{3-bis(3-methyl-4-hydroxyphenyl)methyl-4-carboxymethoxyphenyl}methyl]-4-methyl-1-carboxymethoxybenzene

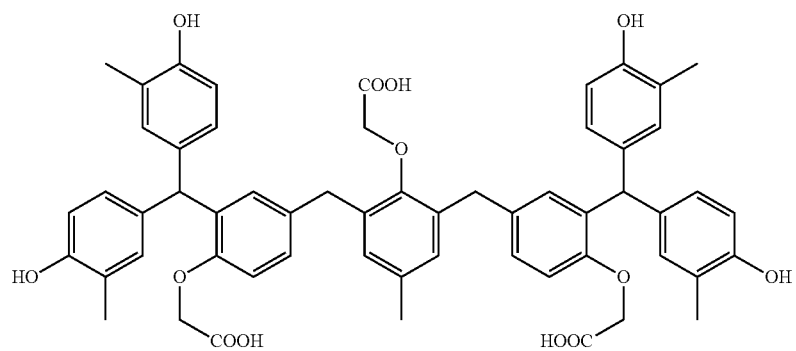 [SMILES: Cc1cc(Cc2ccc(OCC(=O)O)c(C(c3ccc(O)c(C)c3)c3ccc(O)c(C)c3)c2)c(OCC(=O)O)c(Cc2ccc(OCC(=O)O)c(C(c3ccc(O)c(C)c3)c3ccc(O)c(C)c3)c2)c1]

2,6-bis[{3-bis(2-methyl-5-cyclohexyl-4-hydroxyphenyl)methyl-4-carboxymethoxyphenyl}methyl]-4-methyl-1-carboxymethoxybenzene

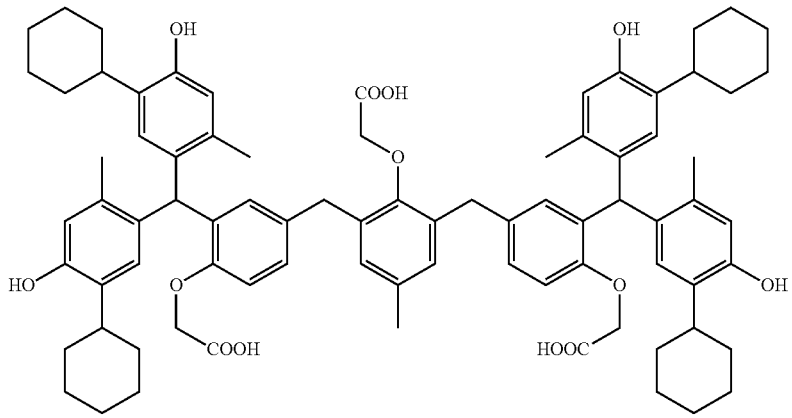 [SMILES: Cc1cc(Cc2ccc(OCC(=O)O)c(C(c3cc(C4CCCCC4)c(O)cc3C)c3cc(C4CCCCC4)c(O)cc3C)c2)c(OCC(=O)O)c(Cc2ccc(OCC(=O)O)c(C(c3cc(C4CCCCC4)c(O)cc3C)c3cc(C4CCCCC4)c(O)cc3C)c2)c1]

Examples of such compound when k is 2 include the following:

Bis[3-{3-bis(2,5-dimethyl-4-hydroxyphenyl)methyl-4-carboxymethoxyphenyl}methyl-2,5-dimethyl-4-carboxymethoxyphenyl]methane Bis[3-{3-bis(2,5-dimethyl-4-hydroxyphenyl)methyl-5-methyl-2-carboxymethoxyphenyl}methyl-5-methyl-2-carboxymethoxyphenyl]methane, 2,6-bis[{3-bis(2-methyl-4,5-dihydroxyphenyl)methyl-2,5-dimethyl-4-carboxymethoxyphenyl}methyl]-4-methyl-1-carboxymethoxybenzene,

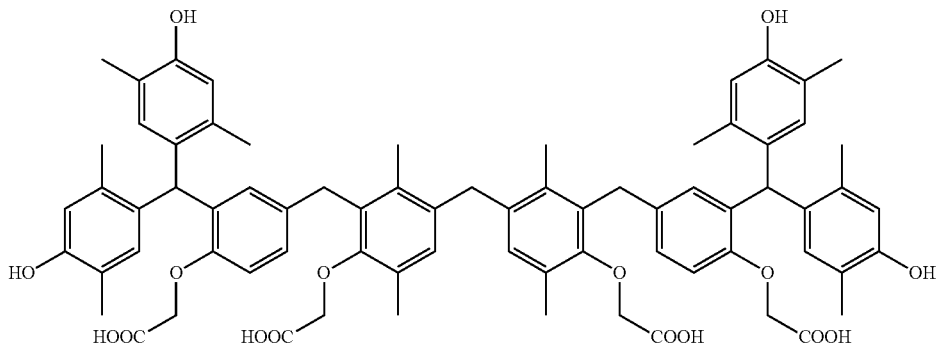 [SMILES: Cc1cc(C(c2cc(C)c(O)cc2C)c2cc(Cc3c(C)c(Cc4cc(C)c(OCC(=O)O)c(Cc5ccc(OCC(=O)O)c(C(c6cc(C)c(O)cc6C)c6cc(C)c(O)cc6C)c5)c4C)cc(C)c3OCC(=O)O)ccc2OCC(=O)O)c(C)cc1O]

Other examples include the following, among others:
2,6-bis[{3-bis(2,3,5-trimethyl-4-hydroxyphenyl)methyl-4-carboxymethoxyphenyl}methyl]-4-methyl-1-carboxymethoxybenzene,
2,6-bis[{3-bis(4-hydroxyphenyl)methyl-4-carboxymethoxyphenyl}methyl]-4-methyl-1-carboxymethoxybenzene,
2,6-bis[{3-bis(3-t-butyl-4-hydroxyphenyl)methyl-4-carboxymethoxyphenyl}methyl]-4-cyclohexyl-1-carboxymethoxybenzene,
2,6-bis[{3-bis(3,5-dimethyl-4-hydroxyphenyl)methyl-4-carboxymethoxyphenyl}methyl]-3,4-dimethyl-1-carboxymethoxybenzene,
2,6-bis[{3-bis(2,5-dimethyl-4-hydroxyphenyl)methyl-4-methoxycarbonylmethoxyphenyl}methyl]-4-methyl-1-methoxycarbonylmethoxybenzene,
2,4-bis[{3-bis(2,5-dimethyl-4-hydroxyphenyl)methyl-4-carboxymethoxyphenyl}methyl]-6-methyl-1-carboxymethoxybenzene, 2,6-bis[{3-bis(2-methyl-4,5-dihydroxyphenyl)methyl-2,5-dimethyl-4-(4-carboxyphenyl)methoxyphenyl}methyl]-4-methyl-1-(4-carboxyphenyl)methoxybenzene,
2,6-bis[{3-bis(2,5-dimethyl-4-hydroxyphenyl)methyl-4-carboxymethoxyphenyl}methyl]-4-methoxy-1-carboxymethoxybenzene,
2,6-bis[{3-bis(3-methoxy-4-hydroxyphenyl)methyl-4-carboxymethoxyphenyl}methyl]-4-methyl-1-carboxymethoxybenzene,
Bis[3-{3-bis(2,5-dimethyl-4-hydroxyphenyl)methyl-4-carboxymethoxyphenyl}methyl-5-methyl-2-carboxymethoxyphenyl]methane, and
Bis[3-{3-bis(2,5-dimethyl-4-hydroxyphenyl)methyl-4-methoxycarbonylmethoxyphenyl}methyl-2,5-dimethyl-4-methoxycarbonylmethoxyphenyl]methane.

Another novel compound proposed by the present invention, or specifically a polynuclear polyphenol compound expressed by general formula (2) above that can be derived from a bis(formylphenyl) compound expressed by general formula (1) above, is not specifically limited in its manufacturing method, but a preferred method to obtain such compound is one where, for example, a bis(formylphenyl) compound expressed by general formula (1) conforming to the present invention is used as the direct material to be reacted with a phenol in the presence of an acid catalyst according to reaction formula (7) below, as illustrated in the example of reaction of 2,6-bis{(3-formyl-4-methoxycarbonylmethoxyphenyl)methyl}-4-methyl-1-methoxycarbonylmethoxybenzene and 2,5-dimethylphenol.

bis(formylphenyl) compound, although a desirable amount to be added varies depending on the phenol used.

Also note that a reaction solvent may or may not be used. However, it is desirable to use a solvent if the mol ratio of the phenol to the bis(formylphenyl) compound is small or the phenol has a high melting point and cannot be mixed easily. Reaction solvents that can be used include, for example, methanol, butanol and other lower aliphatic alcohols, toluene, xylene and other aromatic hydrocarbons, methylisobutylke-

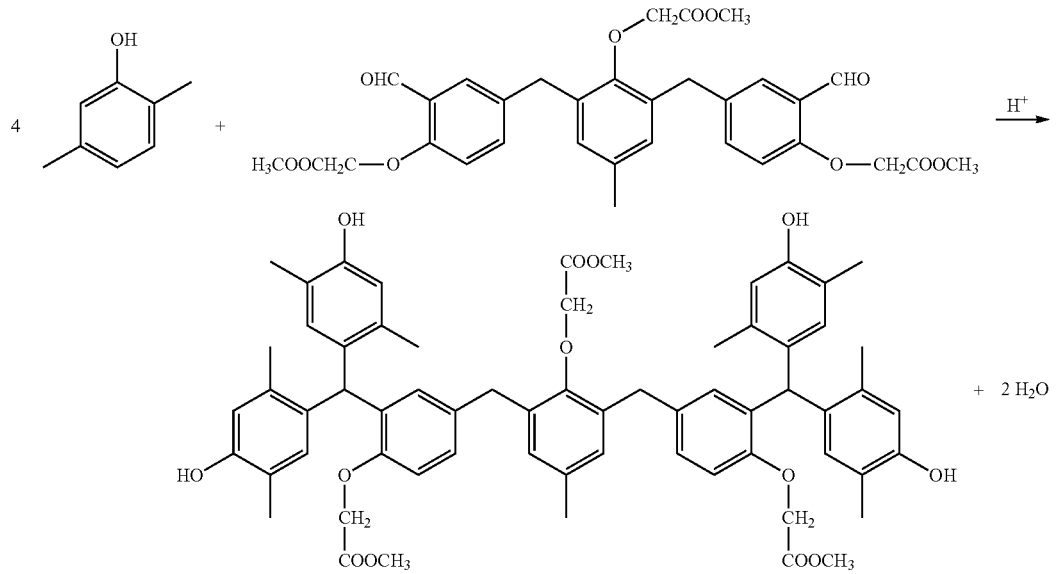

Reaction formula (7)

Among phenols used in the aforementioned example of reaction formula, the phenol expressed by general formula (3) and represented by X in general formula (2) must have at least one of the o-position or p-position of its phenyl core remaining unsubstituted relative to the hydroxyl group substituted to the phenyl core. To be specific, from the viewpoint of synthesis such phenol preferably have its p-position remaining unsubstituted relative to the hydroxyl group if the number of substitution alkyl groups and/or alkoxyl groups is 3 or less and there is one hydroxyl group, or its o-position preferably remain unsubstituted relative to the hydroxyl group if the number of substitution alkyl groups and/or alkoxyl groups is 4.

Specific examples of such phenol include those having one hydroxyl group such as phenol, o-cresol, p-cresol, m-cresol, 2,5-xylenol, 2,6-xylenol, 3,5-xylenol, 2,3,6-trimethylphenol, 2,3,5-trimethylphenol, 2-cyclohexyl-5-methylphenol, 2-cyclohexylphenol, 2-ethylphenol, 2-t-butylphenol, 2-t-butyl-5-methylphenol, 2,4-xylenol, 2,6-di-t-butylphenol, 2,4-di-t-butylphenol, 2-sec-butylphenol, 2-n-octylphenol, 2-t-octylphenol, 4-t-octylphenol, 2-isopropylphenol, 2-t-butyl-4-methylphenol, 2-methoxyphenol, 2-methyl-5-methoxyphenol, 4-butoxyphenol, 2-n-hexyloxyphenol and 2-n-octyloxyphenol, as well as those having two or more hydroxyl groups such as resorcin, catechol, 4-methylcatechol, 3-methylcatechol, 2-methylresorcinol, 4-methylresorcinol and pyrogallol.

As illustrated in the example of reaction formula (7) above, the amount of phenol used in the reaction of bis(formylphenyl) compound and phenol is normally in a range of 4 to 20 mol, or preferably in a range of 4.5 to 10 mol, per 1 mol of tone and other aliphatic ketones, and any mixture solvent comprising the foregoing. Among others, lower aliphatic alcohols are preferred and if catechol, resorcin or other phenol having a high melting point and greater solubility in water is used, water can be used as a reaction solvent.

Although not specifically limited, the use amount of such solvent is normally in a range of 0.5 to 10 parts by weight, or preferably in a range of 0.5 to 2 parts by weight, relative to the phenol used.

In the manufacturing method illustrated in the example of reaction formula (7) above, the acid catalyst is preferably one that dissolves in the reaction mixture liquid, and in this regard an inorganic acid or organic acid such as organic sulfonic acid or carboxylic acid, of strong to medium acidity, is used. Specific examples include 35% hydrochloric acid, hydrogen chloride gas, sulfuric acid, phosphoric acid and other inorganic acids, as well as p-toluenesulfonic acid, methanesulfonic acid, oxalic acid and other organic acids. Although the amount of such acid catalyst used depends on the acidity level and a desirable range varies, normally an acid catalyst is used by an amount in a range of 1 to 50 percent by weight relative to the phenol.

The reaction is normally implemented under agitation in air, or preferably in an atmosphere of nitrogen or other inert gas at a temperature normally in a range of 0 to 100° C. or preferably in a range of 20 to 60° C., normally for a period of 1 to 20 hours.

Under the aforementioned manufacturing method, the polynuclear phenol compound produced by reaction can be separated and refined as necessary according to any known method.

To this end, after the reaction an alkali water such as aqueous sodium hydroxide solution is added to the obtained reaction liquid to neutralize the acid, after which (if necessary, toluene, xylene, methylisobutylketone or ether or other solvent that can be separated from water is added to separate and remove the water layer) the water layer is separated, while the oil layer is washed in water, and if necessary, the solvent or unreacted material phenol is distilled from the obtained oil layer and removed, after which a solvent is added to the distilled residue to crystallize, or precipitate and filter out, a crystalline or non-crystalline solid. If necessary, a similar crystallization or precipitation operation can be repeated once or even more to take out the target at a higher purity.

If the obtained target product is an adduct crystal containing the solvent of low boiling point, the adduct crystal can be broken down under decompression at a temperature of approx. 100 to 200° C. to remove the solvent and thereby refine the target.

If taking out the target polynuclear phenol compound from the reaction product by the aforementioned means of crystallization or precipitation is difficult, column separation may be used to take out and refine the target compound, or in the aforementioned refinement process the solvent may be distilled and removed from the oil layer in which the compound is dissolved in order to take out the target as a resinous substance or composition.

In the case of a polynuclear polyphenol compound expressed by general formula (2) above where $R_4$ is a hydrogen atom and the ether group is a carboxy hydrocarbon substitution product (—$R_3$COOH), the manufacturing method to obtain such compound is not specifically limited. For example, however, the same method used for the bis(formylphenyl) compound can be used, involving ester hydrolysis using an aqueous alkali solution of sodium hydroxide, tetramethylammonium hydroxide, etc., to easily obtain a carboxy hydrocarbon substitution product (—$R_3$COOH) from an alkoxycarbonyl hydrocarbon substitution product (—$R_3$COOR$_4$) where $R_4$ in the alkoxycarbonyl hydrocarbon group (—$R_3$COOR$_4$) of the polynuclear polyphenol compound is a primary alkyl group or secondary alkyl group, as illustrated in the example of reaction formula (8) below.

After the hydrolysis reaction, (if necessary, a solvent that separates from water is added to wash the obtained product) the oil layer is removed. Thereafter, a solvent that separates from water is added, together with an acid, to neutralize the aqueous alkali solution and target alkali salt, after which the water layer is removed and the target is then taken out from the obtained oil layer and refined using a known method like the one mentioned above.

If $R_4$ in the alkoxycarbonyl hydrocarbon group (—$R_3$COOR$_4$) of the bis(formylphenyl) compound expressed by general formula (1) is a tertiaryalkyl group, then $R_4$ in the alkoxycarbonyl hydrocarbon substitution product (—$R_3$COOR$_4$), or specifically the tertiaryalkyl group, is eliminated in the aforementioned reaction of this bis (formylphenyl) compound and phenol, where a carboxy hydrocarbon substitution product (—$R_3$COOH) is produced the moment the bis(formylphenyl) compound reacts with the phenol, and this way a polynuclear polyphenol having such carboxy hydrocarbon substitution product (—$R_3$COOH) can be obtained as illustrated in the example of reaction formula (9) below.

Alternatively, a bis(formylphenyl) compound according to general formula (1) where $R_4$ is a hydrogen atom can be reacted with a phenol to obtain the same.

Reaction formula (8)

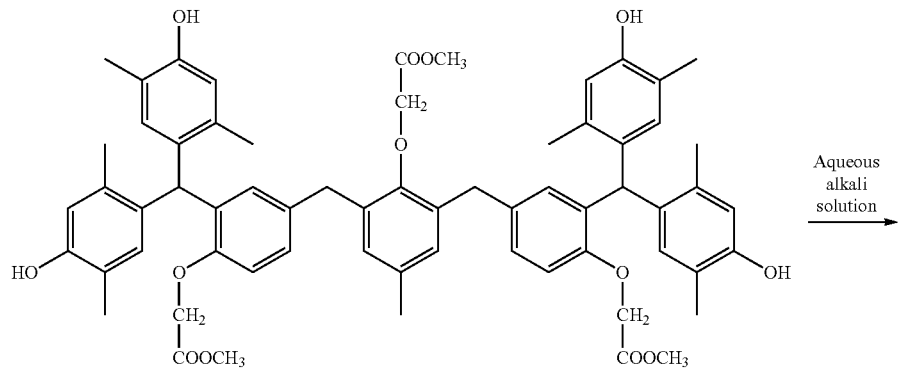

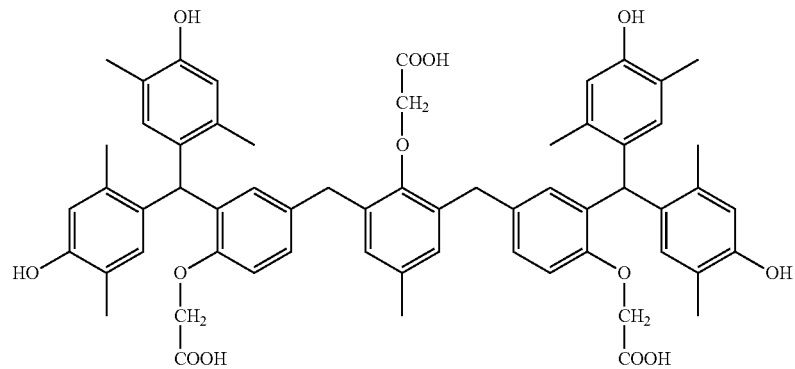

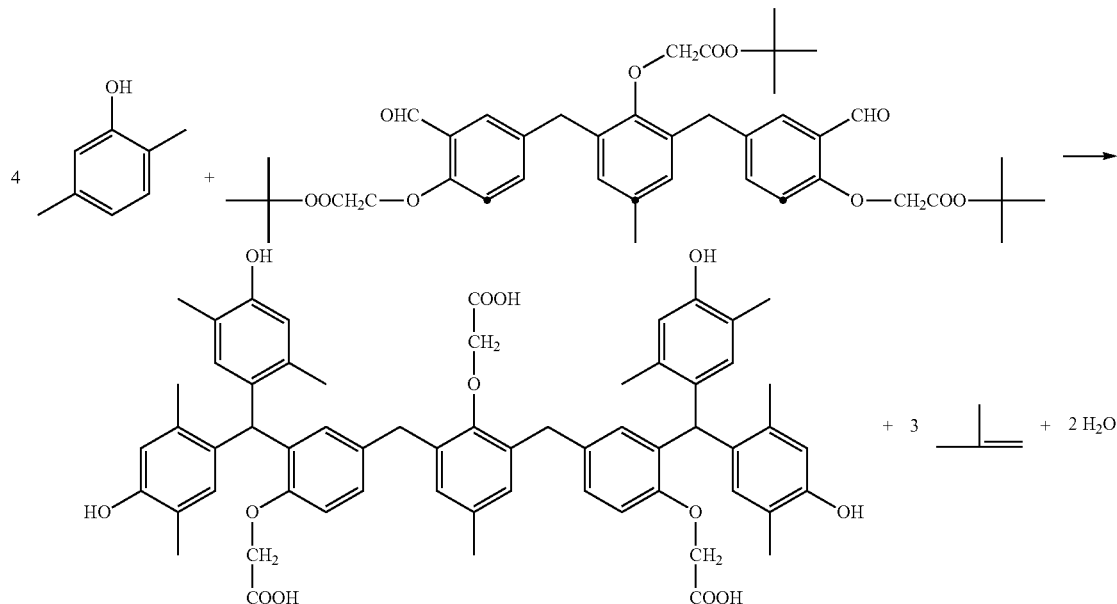

EXAMPLES

The present invention is explained in further details using examples below.

Example 1

Synthesis of bis(formylphenyl) Compound

Synthesis of 2,6-bis{(3-formyl-4-methoxycarbonyl-methoxyphenyl)methyl}-4-methyl-1-methoxycarbonylmethoxybenzene 188.2 g (0.5 mol) of 2,6-bis{(3-formyl-4-hydroxyphenyl)methyl}-4-methylphenol was placed in a four-way flask of 2 liters in capacity and dissolved by adding 470.0 g of N-methylpyrrolidone. The mixture was heated to a temperature of 50° C., after which 28.3 g (0.04 mol) of potassium iodide and 241.8 g (1.76 mol) of potassium carbonate were added and the mixture was agitated for 1 hour. Next, the temperature was raised to 65° C., and then 292.7 g (2.69 mol) of methylchloroacetate was drip-fed over a period of 2 hours, after which the mixture was agitated further for 3 hours at 70° C. After the reaction, 300.0 g of water and 600.0 g of methylisobutylketone were added and the mixture was agitated at 60° C., after which the water layer was removed and 300.0 g of water was further added to repeat water washing and separation three times according to the same operation.

The solvent was distilled from the obtained oil layer under decompression at 70° C., to obtain 240.1 g of liquid with a purity of 78.0% (area %) based on high-speed liquid chromatography.

When a part of this liquid was refined by means of silica gel column chromatography and analyzed by liquid chromatography mass spectrometry and NMR, the liquid was confirmed as the target substance.

Molecular weight (liquid chromatography mass spectrometry/atmospheric pressure chemical ionization method): 593 (M+H)+

Proton NMR analysis (400 MHz, solvent: DMSO-d6, reference substance: tetramethylsilane)

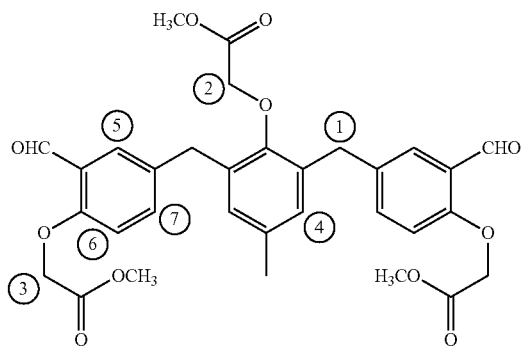

TABLE 1

| Identification results by 1H-NMR (400 MHz) | | | |
|---|---|---|---|
| Shift value (ppm) | Number of protons | Signal | Assignment |
| 2.13 | 3 | s | —CH$_3$ |
| 3.68-3.70 | 9 | m | —OCH$_3$ |
| 3.94 | 4 | s | —CH$_2$① |
| 4.37 | 2 | s | —CH$_2$② |
| 4.94 | 4 | s | —CH$_2$③ |
| 6.83 | 2 | s | Ph—H④ |
| 7.08-7.10 | 2 | d | Ph—H⑤ |
| 7.47-7.50 | 2 | d | Ph—H⑥ |
| 7.57 | 2 | s | Ph—H⑦ |
| 10.41 | 2 | s | —CHO |

Example 2

Synthesis of Polynuclear Polyphenol Compound

Synthesis of 2,6-bis[{3-bis(2,5-dimethyl-4-hydroxyphenyl)methyl-4-carboxymethoxyphenyl}methyl]-4-methyl-1-carboxymethoxybenzene 244.0 g (2.0 mol) of 2,5-xylenol, 135.4 g of methanol and 97.6 g of 35% hydrochloric acid water were placed in a four-way flask of 2 liters in capacity, into which a solution prepared by diluting 237.0 g (0.4 mol) of the bis(formylphenyl) compound obtained in Example 1 with 153.0 g of methanol was drip-fed over a period of 2.5 hours at a temperature of 40° C. under agitation, after which the mixture was agitated further at 50° C. for 16 hours to cause reaction.

After the reaction, 270.0 g of 16% aqueous sodium hydroxide solution was added to neutralize the reaction mixture, which was then condensed at normal pressure to remove 325.9 g of solvent. The remaining liquid was mixed with 800 g of methylisobutylketone and 400 g of water, and the mixture was heated to 70° C. under agitation, and then kept stationary for 10 minutes, after which the water layer was removed and 400 g of water was added to the obtained oil layer to perform water washing and separation according to the same operation.

Next, 1005 g of 25% aqueous tetramethylammonium hydroxide solution was added to the obtained oil layer and the mixture was hydrolyzed for 30 minutes at 70° C. under agitation, after which the oil layer (upper layer) was removed. The obtained water layer was then neutralized at 50° C. by adding 910.0 g of methylisobutylketone and 288.0 g of 35% aqueous hydrochloric acid solution. Next, the water layer was removed, 400 g of water was added, and the mixture was heated to 70° C. under agitation to remove the water layer. The obtained oil layer was then condensed under decompression to remove 788.1 g of solvent, and the remaining liquid was mixed with 197.8 g of acetone and 397.8 g of toluene in this order (crystal precipitated when acetone was added). The slurry was cooled and then filtered to obtain 302.4 g of crude crystal.

The obtained crude crystal was dissolved in 834.6 g of methylisobutylketone and 834.6 g of methylethylketone, and the mixture was condensed under decompression to remove 1309.1 g of solvent (crystal precipitated during this process), after which 471.9 of toluene was added.

The mixture was cooled and filtered and the obtained crystal was dried at 120° C. under decompression to obtain 221.3 g of the target light-yellow powder of 95.5% (area %) in purity based on high-speed liquid chromatography.

The yield relative to the material bis(formylphenyl) compound was 50.3%.

Glass transition temperature: 128.1° C. (differential scanning calorimetry, peaktop)

Molecular weight (liquid chromatography mass spectrometry/atmospheric pressure chemical ionization method): 1002 (M–H)⁻

Proton NMR analysis (400 MHz, solvent: DMSO-d6, reference substance: tetramethylsilane)

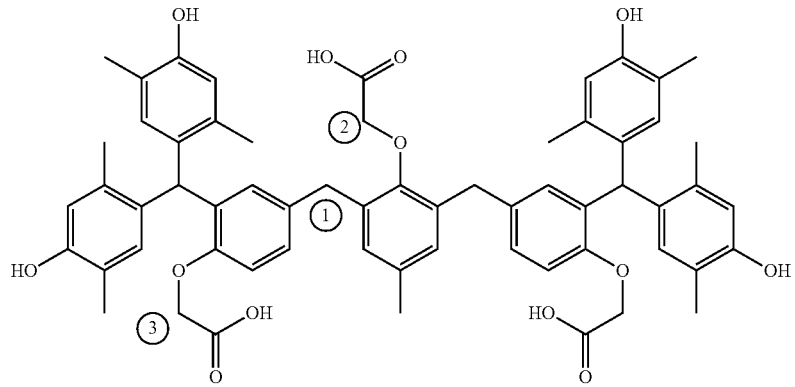

TABLE 2

Identification results by 1H-NMR (400 MHz)

| Shift value (ppm) | Number of protons | Signal | Assignment |
|---|---|---|---|
| 1.91-2.29 | 27 | m | —CH₃ |
| 3.78 | 4 | s | —CH₂① |
| 4.02 | 2 | s | —CH₂② |
| 4.51 | 4 | s | —CH₂③ |
| 5.87 | 2 | s | —CH |
| 6.35-7.26 | 16 | m | Ph—H |
| 7.57 | 4 | s | Ph—OH |
| 12.81 | 3 | s | —COOH |

Reference Example 1

Synthesis of Material bis(hydroxy-formylphenyl) Compound

Synthesis of bis[3-(3-formyl-4-hydroxyphenyl)methyl-2,5-dimethyl-4-hydroxyphenyl]methane 146.4 g (1.2 mol) of salicylaldehyde and 146.4 g of 75% aqueous phosphoric acid solution were placed in a four-way flask of 1 liter in capacity and the interior of the flask was replaced by nitrogen, after which 63.3 g (0.2 mol) of bis(2,5-dimethyl-3-hydroxymethyl-4-hydroxyphenyl)methane was added at 60° C. over a period of 5 hours under agitation to cause reaction. When the reaction was continued at 60° C. for 4 hours under agitation, crystal precipitated in the middle of reaction.

After the reaction, 10.0 g of methylisobutylketone and 100.0 g of toluene were added to the reaction liquid and the mixture was cooled to 25° C., after which the precipitated crystal was filtered out to obtain 83.4 g of crystalline product.

Next, the obtained product was placed in a four-way flask of 1 liter in capacity together with 140.0 g of methylethylketone, 260.0 g of methylisobutylketone and 80.0 g of water, and then the mixture was heated to 60° C. to dissolve the product, after which the mixture was kept stationary to remove the water layer. The obtained oil layer was heated at 65° C. under decompression to distill 328.1 g of solvent, after which 80.0 g of toluene was added to cause crystal to precipitate. Thereafter, the mixture was cooled to 25° C. and filtered to obtain 29.7 g of crystalline product.

The product obtained above was placed in a four-way flask of 1 liter in capacity together with 75.0 g of methylisobutylketone, and the mixture was heated to 60° C. under agitation and then the resulting slurry was cooled to 25° C. Thereafter, the mixture was filtered and dried to obtain 13.0 g of the target light-yellow powder (of 91.1% in purity based on high-speed liquid chromatography). The yield relative to the material hydroxymethyl substituted bisphenol was 12.4%.

1H-NMR (400 MHz), solvent: DMSO-d6, reference substance: tetramethylsilane

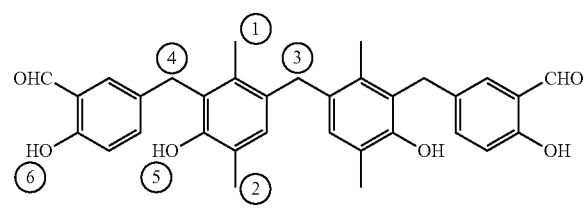 [SMILES: Cc1cc(Cc2cc(C)c(O)c(Cc3ccc(O)c(C=O)c3)c2C)c(C)c(Cc2ccc(O)c(C=O)c2)c1O]

TABLE 3

| Identification results by 1H-NMR (400 MHz) | | | |
|---|---|---|---|
| Shift value (ppm) | Number of protons | Signal | Assignment |
| 1.98-2.08 | 12 | m | —CH₃ (①+②) |
| 3.67 | 2 | s | —CH₂③ |
| 3.99 | 4 | s | —CH₂④ |
| 6.45-7.37 | 8 | m | Ph—H |
| 8.04 | 2 | s | Ph—OH⑤ |
| 10.21 | 2 | s | Ph—OH⑥ |
| 10.47 | 2 | s | —CHO |

Example 3

Synthesis of bis(formylphenyl) Compound

Synthesis of bis{3-(3-formyl-4-methoxycarbonyl-methoxyphenyl)methyl-2,5-dimethyl-4-methoxycarbonylmethoxyphenyl}methane 12.6 g (2.4×10⁻² mol) of the bis(formylphenol) compound obtained in Reference Example 1 and 31.5 g of N-methyl pyrrolidone were placed in a four-way flask of 500 ml in capacity and dissolved, after which the interior of the flask was replaced by nitrogen. The obtained solution was heated to 50° C., and then 1.9 g (1.1×10⁻² mol) of potassium iodide and 16.6 g (0.12 mol) of potassium carbonate were added and the mixture was agitated for 1 hour.

Next, the mixture was heated to 60° C., and then 20.8 g (0.19 mol) of methylchloroacetate was drip-fed over a period of 2 hours 30 minutes under agitation to cause reaction, which was continued at 60° C. for another 6 hours under agitation.

After the reaction, 64.0 g of methylisobutylketone and 20 g of water were added to the reaction liquid and the mixture was agitated and then kept stationary to remove the water layer. The obtained oil layer was then mixed with 20.0 g of water to perform water washing and removal of water layer three times according to the same operation.

The obtained oil layer was heated to 70° C. under decompression to distill the solvent, to obtain 19.1 g of viscous liquid (of 87.5% in purity based on high-speed liquid chromatography). According to liquid chromatography mass spectrometry and NMR analysis, the obtained liquid was confirmed to be the target compound expressed by the chemical formula below.

The yield relative to the material bis(formylphenol) compound was 97.9%.

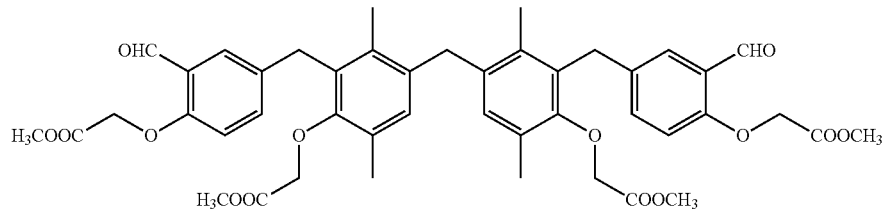

Example 4

Synthesis of Polynuclear Polyphenol Compound

Synthesis of bis[3-{3-bis(2,5-dimethyl-4-hydroxyphenyl)methyl-4-carboxymethoxyphenyl}methyl-2,5-dimethyl-4-carboxymethoxyphenyl]methane 14.3 g (0.12 mol) of 2,5-xylenol and 14.3 g of methanol were placed in a four-way flask of 500 ml in capacity and dissolved, after which the interior of the flask was replaced by nitrogen and then 5.7 g of 35% hydrochloric acid water was added, into which a solution prepared by diluting 19.1 g (2.35×10⁻² mol) of the bis(formylphenyl) compound obtained in Example 3 with 15.0 g of toluene was drip-fed at 40° C. over a period of 1.5 hours under agitation to cause reaction, which was continued at 50° C. for another 21 hours under agitation.

After the reaction, 19.6 g of 25% aqueous tetramethylammonium hydroxide solution was added to the reaction mixture to neutralize the mixture, which was then heated at normal pressure to distill 30.6 g of solvent.

Then, 57.0 g of methylisobutylketone and 30.0 g of water were added and the mixture was heated to 70° C. under agitation and then kept stationary to remove the water layer. The obtained oil layer was mixed with 30.0 g of water to perform water washing and removal of water layer according to the same operation. The obtained oil layer was mixed with 59.8 g of 25% aqueous tetramethylammonium hydroxide solution and the mixture was hydrolyzed at 60° C. for 1 hour under agitation, and then kept stationary to remove the upper layer, after which the obtained water layer and 42.0 g of methylisobutylketone were mixed at 50° C. and then 17.2 g of 35% aqueous hydrochloric acid solution was added under agitation, and then the mixture was kept stationary to remove the water layer.

50.0 g of water was added to the obtained oil layer and the mixture was heated to 70° C. under agitation, after which the water layer was removed and the obtained oil layer was heated under decompression to remove the solvent and thereby obtain 23.0 g of solid of reddish brown color.

Next, the obtained solid was dissolved in 30 g of methylisobutylketone and the obtained solution was drip-fed into 500.0 g of toluene to cause precipitation again, and the precipitated solid was filtered and dried to obtain 20.4 g of the target light-yellow powder (of 89.8% in purity based on high-speed liquid chromatography). The yield relative to the material bis(formylphenyl) compound was 71.8%.

Glass transition temperature: 151.7° C. (DSC)
Molecular weight: 1208.4 (M−H)⁻ (liquid chromatography mass spectrometry/atmospheric pressure chemical ionization method)
1H-NMR (400 MHz), solvent: DMSO-d6, reference substance: tetramethylsilane

What is claimed is:
1. A polynuclear polyphenol compound expressed by general formula (2) below:

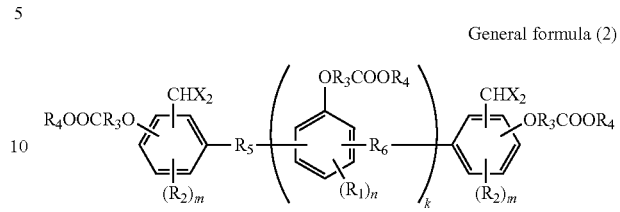

General formula (2)

wherein $R_1$ and $R_2$ each independently represent an alkyl group with 1 to 8 carbon atoms or alkoxyl group with 1 to 8 carbon atoms, $R_3$ is an aliphatic saturated hydrocarbon group with 1 to 8 carbon atoms that may have a single-ring or condensed-ring aromatic hydrocarbon group with 6 to 15 carbon atoms, $R_4$ is a hydrogen atom or primary alkyl group or secondary alkyl group with 1 to 6 carbon atoms, $R_5$ and $R_6$ may be the same or different and each represent a bivalent aliphatic saturated hydrocarbon group with 1 to 8 carbon atoms, m is an integer of 0 or 1 to 3, n is an integer of 0 or 1 to 3, and k is an integer of 1 to 3, but if k is 2 or greater, then $R_6$, $R_1$ and n in each phenyl group may all be the same or different, and X is a hydroxyphenyl group expressed by general formula (3) below:

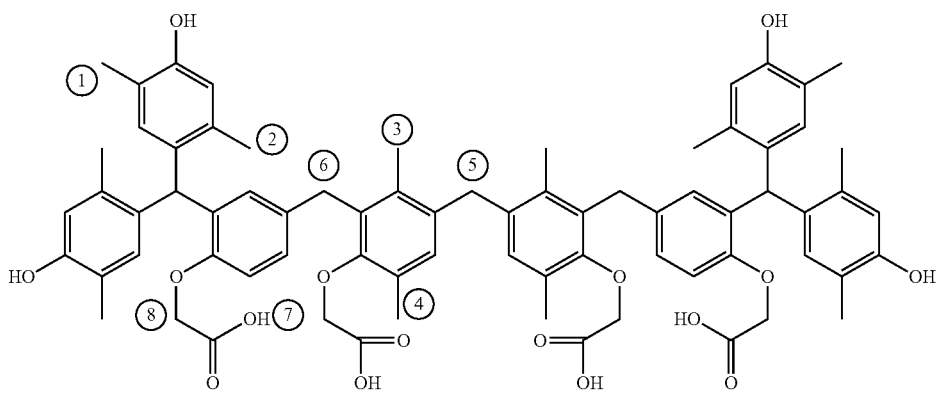

TABLE 4

Identification results by 1H-NMR (400 MHz)

| Shift value (ppm) | Number of protons | Signal | Assignment |
|---|---|---|---|
| 1.83-2.02 | 36 | m | —CH₃ (①+②+③+④) |
| 3.70 | 2 | s | —CH₂⑤ |
| 3.81 | 4 | s | —CH₂⑥ |
| 3.96 | 4 | s | —CH₂⑦ |
| 4.50 | 4 | s | —CH₂⑧ |
| 5.80 | 2 | s | —CH |
| 6.20-6.95 | 16 | m | Ph—H |
| 8.83 | 4 | s | Ph—OH |
| 12.76 | 4 | s | —COOH |

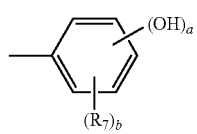

General formula (3)

wherein $R_7$ is an alkyl group with 1 to 8 carbon atoms or alkoxyl group with 1 to 8 carbon atoms, a is an integer of 1 to 3, b is an integer of 0 to 4, where 1≤a+b≤5, and if b is 2 or greater, then $R_7$'s may be the same or different.

2. A polynuclear polyphenol compound according to claim 1, wherein the hydroxyphenyl group in general formula (3) above is expressed by general formula (4) below:

General formula (4)

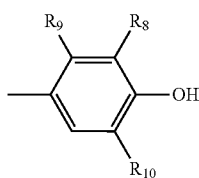

wherein $R_8$, $R_9$ and $R_{10}$ each independently represent a hydrogen atom or alkyl group with 1 to 8 carbon atoms or alkoxyl group with 1 to 8 carbon atoms.

3. A polynuclear polyphenol compound according to claim 1, which is expressed by formula (11) below:

General formula (11)

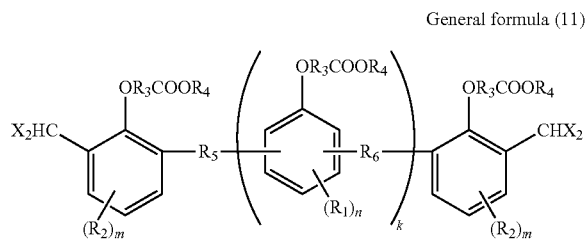

wherein $R_1$ to $R_6$, X, k, m and n are the same as the corresponding items in general formula (2), respectively.

4. A method of producing a polynuclear polyphenol compound according to claim 1, comprising:
reacting a bis(formylphenyl) compound expressed by general formula (1) below as a direct material with a hydroxyphenyl group expressed by general formula (3) in the presence of an acid catalyst:

General formula (1)

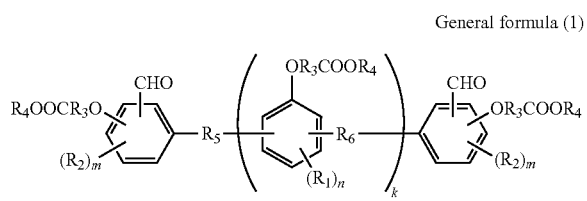

wherein $R_1$ and $R_2$ each independently represent an alkyl group with 1 to 8 carbon atoms or alkoxyl group with 1 to 8 carbon atoms, $R_3$ is an aliphatic saturated hydrocarbon group with 1 to 8 carbon atoms that may have a single-ring or condensed-ring aromatic hydrocarbon group with 6 to 15 carbon atoms, $R_4$ is a hydrogen atom or alkyl group with 1 to 6 carbon atoms, $R_5$ and $R_6$ may be the same or different and each represent a bivalent aliphatic saturated hydrocarbon group with 1 to 8 carbon atoms, m is an integer of 0 or 1 to 3, n is an integer of 0 or 1 to 3, and k is an integer of 1 to 3, but if k is 2 or greater, then $R_6$, $R_1$ and n in each phenyl group may all be the same or different.

5. A polynuclear polyphenol compound according to claim 1, which has the following formula:

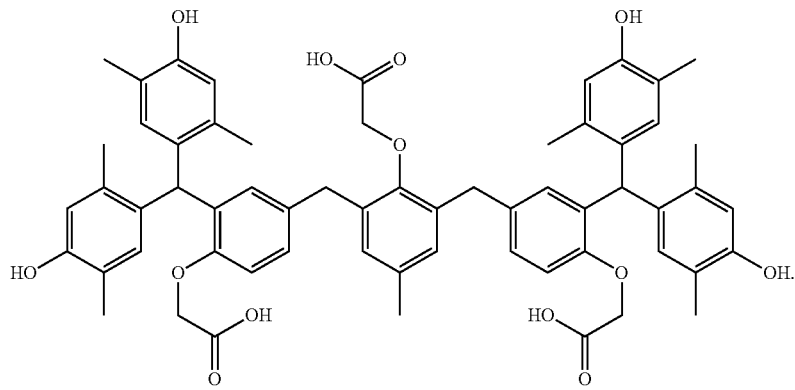 [SMILES: Cc1cc(Cc2ccc(OCC(=O)O)c(C(c3cc(C)c(O)cc3C)c3cc(C)c(O)cc3C)c2)c(OCC(=O)O)c(Cc2ccc(OCC(=O)O)c(C(c3cc(C)c(O)cc3C)c3cc(C)c(O)cc3C)c2)c1]

* * * * *